United States Patent [19]

Brown

[11] Patent Number: 5,151,314
[45] Date of Patent: Sep. 29, 1992

[54] THREE-LAYER LAMINATED PANEL
[75] Inventor: Craig C. Brown, Arlington, Tex.
[73] Assignee: Johnson & Johnson Medical, Inc., Arlington, Tex.
[21] Appl. No.: 648,715
[22] Filed: Jan. 31, 1991
[51] Int. Cl.$^5$ ............................................... B32B 27/14
[52] U.S. Cl. .................................... 428/198; 128/849; 428/131; 428/137; 428/138; 428/171; 428/172; 428/247; 428/284; 428/286; 428/913
[58] Field of Search ............... 428/198, 284, 286, 170, 428/171, 172, 913, 131, 137, 138, 247; 128/849

[56] References Cited

U.S. PATENT DOCUMENTS

| | | | |
|---|---|---|---|
| 3,137,746 | 6/1964 | Seymour et al. | 264/73 |
| 4,275,105 | 6/1981 | Boyd et al. | 428/198 |
| 4,433,026 | 2/1984 | Molde | 428/252 |
| 4,616,644 | 10/1986 | Saferstein et al. | 128/156 |
| 4,622,036 | 11/1986 | Goodrum | 604/367 |
| 4,710,186 | 12/1987 | DeRossett et al. | 604/383 |
| 4,781,962 | 11/1988 | Zamarripa et al. | 428/171 |

*Primary Examiner*—James J. Bell

[57] ABSTRACT

A three-layer laminated material is particularly useful for surgical drape reinforcing panels. The material has a first outer layer of liquid impervious material, an intermediate layer of absorbent material, and a second outer layer of plastic webbing. The webbing layer, which is on top when a drape covers a recumbent person, reduces linting from the absorbent layer without substantially reducing absorbency. The webbing layer is secured to the absorbent layer by a cold cure adhesive. In preferred embodiments, one or both of the outer layers are corona-treated materials and the intermediate layer is a nonwoven fabric.

13 Claims, 2 Drawing Sheets

THREE-LAYER LAMINATED PANEL

BACKGROUND OF THE INVENTION

1. Field of the Invention

The present invention relates generally to laminated materials comprising a layer of nonwoven fabric which is capable of absorbing liquids and a layer of plastic film which is impermeable to liquids. More particularly, the invention relates to laminated materials having improved resistance to "linting", which is loss of fiber from the nonwoven fabric portion of the laminate during handling or use thereof. Even more particularly, the invention relates to laminated materials which can be advantageously used as reinforcing materials for surgical drapes. Surgical drapes employing the laminated material of the present invention have increased structural integrity in the region where the laminate is used; good absorption of liquids such as water, blood, alcohol, and the like, which are commonly encountered during surgery; and a significantly reduced tendency to "lint" or shed fibers or fiber fragments during handling or use. The latter feature is particularly important in view of the desire to prevent to the extent possible foreign materials such as fibers or fiber fragments, from reaching the surgical site.

2. Description of the Related Art

Disposable surgical drapes comprising main sheets of plastic film or nonwoven fabric have been known and used for a number of years. These drapes, which are generally supplied to the end-user in a sterilized condition, are large enough to cover the patient about to undergo surgery and to extend over the sides and usually one end of the operating table toward the floor. Such draping of the patient and operating table provides a "sterile field" and helps isolate the patient from undesirable contamination by foreign materials.

Disposable surgical drapes are very often fenestrated; i.e., they are provided with a fenestration or opening through which the surgery is actually performed. Such fenestrations are usually provided at the time of manufacture of the drape. Some surgical drapes, however, are not provided with a fenestration at the time of manufacture. In such instances, a member of the surgical team will provide a fenestration by cutting away portions of the drape at the region where it is desired to have the fenestration.

It is also known, especially where the main sheet of a surgical drape comprises a nonwoven fabric, to provide the drape with a reinforcing panel in the region surrounding the aforementioned fenestration or the region where such fenestration will be made by the surgical team. Prior art reinforcing materials or panels have utilized a layer of absorbent material, such as a nonwoven fabric, foam or tissue, laminated to a layer of liquid impermeable material such as polyethylene film. The reinforcing material is secured to the upper surface of the main sheet of the drape around the site of the fenestration so that its liquid impermeable layer faces the main sheet and its absorbent layer remains exposed so that it will face upwardly when the patient is draped. The reinforcing panel itself has typically been secured to the main sheet by the use of a continuous layer of a suitable adhesive.

A surgical drape having a reinforcing panel of the type just described has improved structural integrity resulting from the fact that there are additional layers of material in the reinforced region and because of the presence of the fluid impermeable plastic film layer in the reinforcing panel. The absorptive upper surface of the reinforcing panel serves to absorb and retain the various liquids, such as blood and irrigating fluids, which are encountered at the surgical site and prevent the same from pooling on the drape or running from the surface thereof onto the floor or the clothing of the medical personnel in attendance. Additionally, the liquid impervious layer of the reinforcing panel prevents liquids which are captured by the absorbent layer from undesirably penetrating the underlying portion of the main sheet of the drape and contacting the body of the patient.

One prior art method which has been used to make the reinforcing panel is extrusion lamination, in which the liquid-impermeable material, e.g. polyethylene, is extruded directly onto one major surface of the liquid absorbent layer. Typically, lamination is accomplished at temperatures in the range 450°–550° F. (232°–288° C.), with nip pressures between 20 and 50 lb/in$^2$ (138–345 kN/m$^2$). The surface fibers comprising the absorbent layer are coated with and become embedded in the extruded polyethylene layer, thereby forming a laminated material in which the liquid absorbent layer is secured to the liquid impermeable layer.

In another prior art method of making a reinforcing panel (adhesion lamination), a layer of pressure-sensitive adhesive is applied to one surface of either the absorbent layer or the liquid-impermeable layer and the two layers are fed through the nip of a pair of pressure rollers at ambient temperature. The layers are typically laminated at nip pressures of 10–20 lb/in$^2$ (69–138 kN/m$^2$).

Preparation of reinforcing panels by the aforementioned prior art methods tends to undesirably stiffen the panel and reduce the liquid absorbing capacity of the absorbent layer. This is because some of the fibers constituting the absorbent layer are embedded in or are partially or fully coated by the material used for the liquid-impermeable layer and/or by the adhesive.

A decrease in the absorptive capacity of the reinforcing panel is undesirable in that it tends to reduce the ability of the drape to control fluids at the operative site and because it may, in extreme cases, lead to pooling of fluids on the surface of the drape. In addition, many reinforcing panels contain an antimicrobial agent to kill microbes which may be carried in body fluids, irrigating fluids and the like encountered during surgery. These microbes are killed when the liquids carrying them are brought into contact with the antimicrobial agent in the absorbent layer of the reinforcing panel. Thus, if the absorbency of the reinforcing panel is reduced, the bacteria may not be brought as quickly into contact with the bacteriocidal agent and the bacteria may not be killed as quickly as would otherwise be possible.

Another problem which has been experienced with reinforcing panels of the prior art is that known as "linting". This is the shedding, during pre-operative handling or actual use of the drape, of fibers or fiber fragments from the absorbent layer comprising the reinforcing panel. It is, of course, desirable to minimize linting in order to keep foreign particles from contaminating the environs of the operating room or the site of the surgical incision.

SUMMARY OF THE INVENTION

In accordance with one aspect of the present invention, there is provided a reinforcing panel having excellent liquid absorption characteristics and a reduced tendency to lint. This reinforcing panel comprises a three-layered or "tricomponent" laminate which includes a first outer layer of liquid impervious material, an intermediate layer of absorbent material, and an upper or second outer layer of an open, porous web or net-like plastic material.

In accordance with another aspect of the present invention, there is provided a disposable surgical drape comprising a main sheet of plastic or nonwoven material and a reinforcing panel made of the aforementioned three-layered, or tricomponent, laminate. The first outer layer of the reinforcing panel is secured to the top surface of the drape in a region within which surgery is to be performed. The top surface is that which is up when the drape covers a recumbent person.

DETAILED DESCRIPTION OF THE INVENTION

The present invention provides a tricomponent laminated reinforcing Panel for a surgical drape that provides reduced linting, without sacrificing absorbency.

Figure 1:
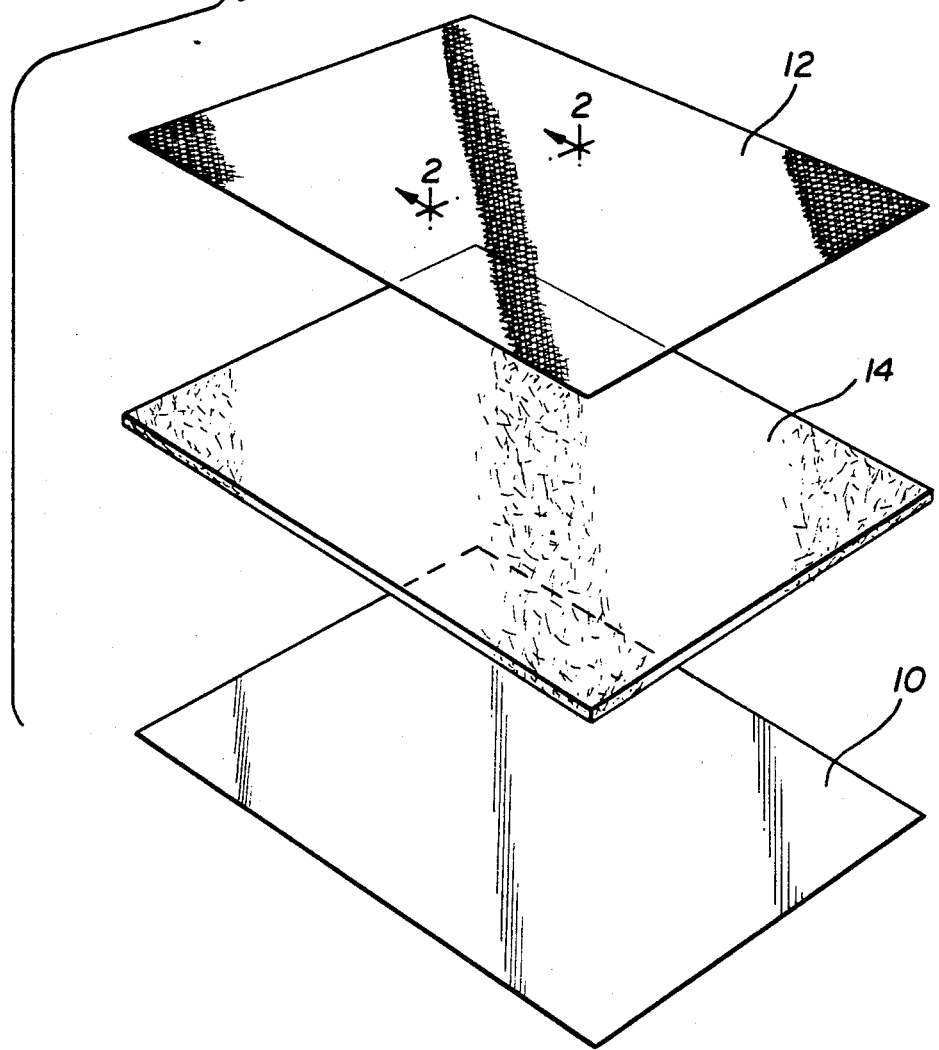
FIG. 1 is an exploded view of a tricomponent laminate of the present invention.

FIG. 1 depicts an exploded view of the structure of a tricomponent laminate of this invention. A first outer layer 10 of liquid impervious material and a second outer layer 12 of net-like plastic sandwich an absorbent intermediate layer 14 The liquid impervious material 10 preferably comprises a liquid impermeable plastic such as polyethylene, while the absorbent intermediate layer 14 is preferably a nonwoven fabric. Preferably, the absorbent material incorporates an antimicrobial agent of a type well known in the art.

Figure 2:
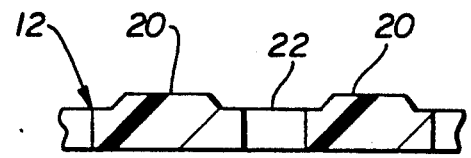
FIG. 2 is a cross-sectional view taken along line 2—2 of FIG. 1.

FIG. 2 shows in cross section the open, porous net-like plastic material comprising the upper, or second, outer layer 12. This layer comprises a plurality of raised bosses 20 joined to each other by strands or filaments of plastic material 22. These net-like plastic materials, which are known per se. are disclosed in, e.g., U.S. Pat. No. 3,137,746, issued Jun. 16, 1964, to D. E. Seymour et al., the disclosure of which is incorporated herein by reference. The net-like plastic materials are preferably nonwovens, such as those available commercially from Applied Extrusion Technologies, Inc., Middletown, Del., USA, under the trademark "Delnet*". It will be understood that the liquid-absorbent layer of the tricomponent laminate is "sandwiched" between the lower, or first outer layer of liquid-impermeable material and the upper, or second, outer layer of the aforementioned net-like material. Before lamination, the first and second plastic outer layers are preferably corona-treated, by methods well known in the art, except that the roll is preferably a ceramic back-up roll, to resist being burned by the corona. The second outer layer is adhered to the absorbent intermediate layer with a cold cure adhesive, by which is meant an adhesive that does not need to be cured at temperatures above ambient. Preferably, the adhesive is a moisture-cured polyurethane adhesive, more preferably the adhesive has a microfiber structure that tends to avoid plugging the open areas of the second outer layer. Plugging these areas causes undesirably reduced absorbent capacity and/or rate of absorbency. Plugging is also avoided by putting down a dot pattern of adhesive, surrounded by adhesive-free areas, so that the adhesive covers less than half the total area. It has been found, quite unexpectedly, that the upper layer of net-like plastic material greatly reduces linting of the underlying absorbent material without significantly reducing its absorbent properties.

Figure 3:
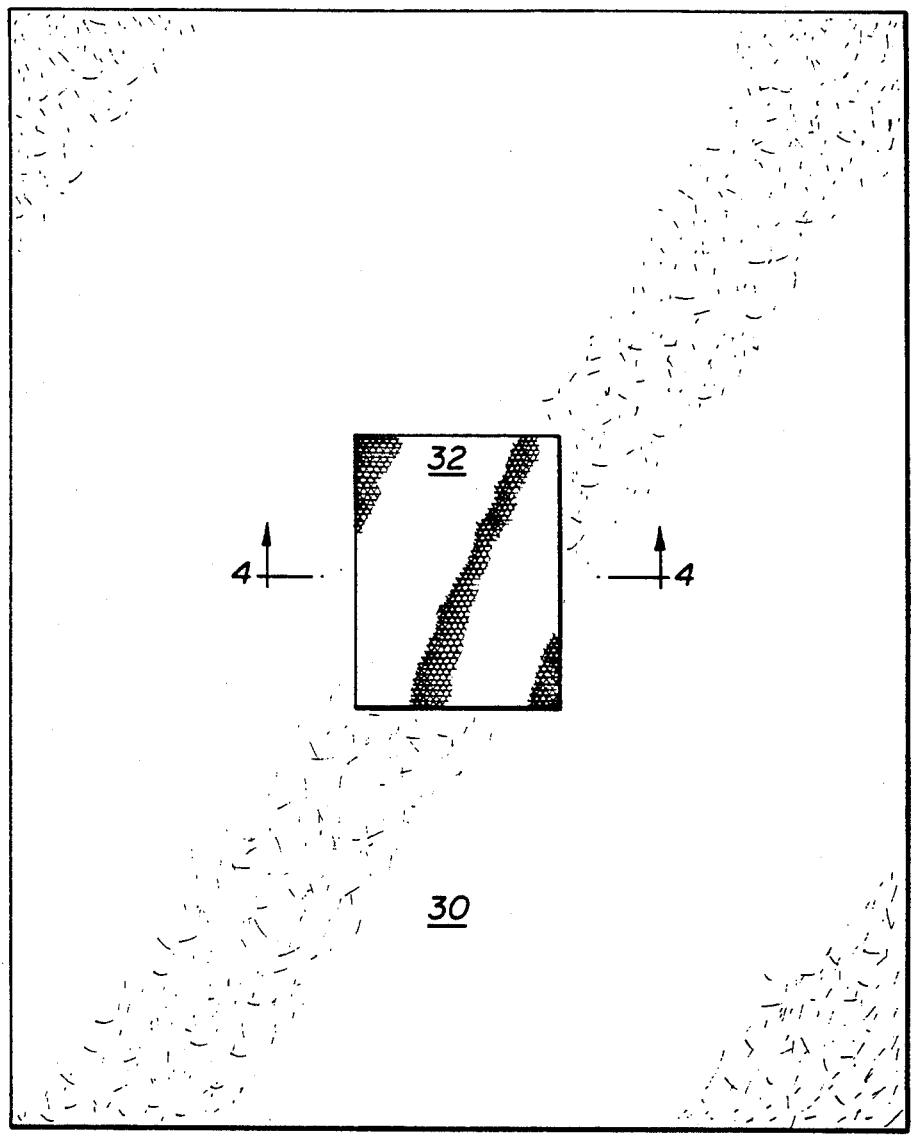
FIG. 3 is a plan view of a surgical drape with reinforcing panel of the present invention.

FIG. 3 is a plan view of the reinforcing panel of the present invention used in conjunction with a surgical drape. As will be understood by those skilled in the art, the main sheet 30 of a surgical drape is generally quite large since, as mentioned, it is used to cover not only the patient about to undergo surgery but also the sides and usually one end of the operating table. For example, the main sheet 30 of a disposable surgical drape intended for use on an adult patient might typically have a width ranging from 60–80 inches (152 to 203 cm) and a length ranging from 100–120 inches (254 to 305 cm). On the other hand, a reinforcing panel 32 may have dimensions that are considerably smaller than those of the main sheet which comprises the surgical drape. As indicated, these reinforcing panels are used to reinforce the main sheet in the regions where, or through which, surgery is to take place.

Figure 4:
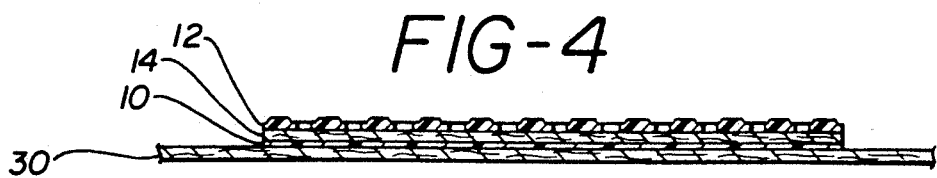
FIG. 4 is a cross-sectional view taken along line 4—4 of FIG. 3.

FIG. 4 shows a reinforcing panel and drape of FIG. 3 in cross section. This four-layer construction includes the drape 30, first outer layer 10, intermediate absorbent layer 14 and second outer layer 12. Usually, although not necessarily, reinforcing panels are placed inwardly of the perimetric edges of the main sheet. In a typical surgical drape for abdominal surgery, the reinforcing panel would be uniformly spaced from the longitudinal side edges of the main sheet and would be spaced somewhat closer to the top edge than the bottom edge of the main sheet. The size and shape of reinforcing panels can very widely. Very frequently, a reinforcing panel is rectangular in shape, with its width ranging from about 12 to about 15 inches (31 to 38 cm) and its length ranging from about 18 to about 95 inches (46 to 241 cm). A surgical drape, depending upon its intended use, may comprise one or more reinforcing panels.

Figure 5:
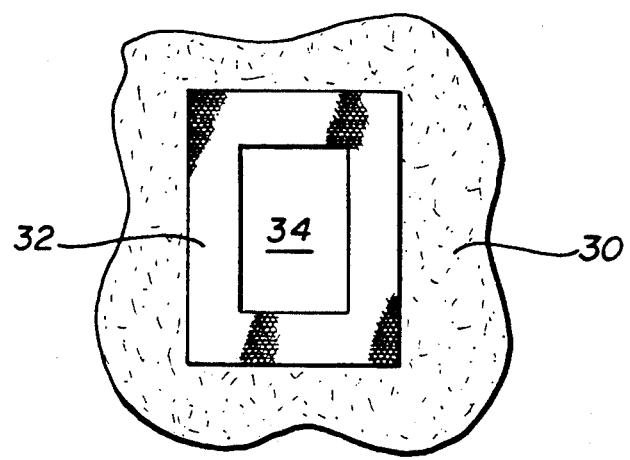
FIG. 5 is a partial view of another embodiment of a reinforcing panel of the present invention.

As indicated previously, surgical drapes may be provided with fenestrations, or openings, therein. FIG. 5 is a partial plan view of a drape 30 and panel 32 having a fenestration 34. The fenestration may be provided by the supplier during the manufacturing process or by the surgical team just prior to surgery. In either case it will be understood by those skilled in the art that such fenestrations are usually surrounded by the reinforcing material.

EXAMPLE 1

A tricomponent laminate in accordance with the present invention was prepared as follows. A 65% solids room temperature curable polyurethane adhesive available from Mace Adhesive and Coating Company under the designation Mace #6800 was applied to a first sheet of silicone release paper at the rate of 9 g/m² using a hand-held No. 180 Gravure coating roller, obtained from Modern Engraving and Machine Company. The roller had a trihelical pattern and a cell volume of 6.7×10$^9$ cubic micrometers. The adhesive was immediately transfer-coated onto a liquid impermeable, corona treated, low density polyethylene film having a thickness of 1.25 mils (49 micrometers). The resulting film/adhesive combination was then laminated using light hand pressure to a liquid absorbent nonwoven fabric to give a bicomponent laminate. The nonwoven fabric had a thickness of about 0.75 mm and weighed 1.6 oz/yd$^2$ (54 g/m$^2$). The nonwoven fabric comprised a lower layer of woodpulp fibers and an upper veneer layer of rayon fibers having a denier of 1.5. The layer of woodpulp fibers was about 0.675 mm thick and had a weight of about 1.4 oz/yd$^2$ (47 g/m$^2$). The rayon fiber veneer layer was about 0.075 mm in thickness and had a density of about 0.2 oz/yd$^2$ (7 g/m$^2$). The length of the rayon fibers in the veneer layer was about 0.5 inch (1.3 cm). The nonwoven fabric also comprised a polymeric binder in the amount of about 25% based on the weight of the fibers. The nonwoven fabric was laminated to the adhesive-coated polyethylene film so that the woodpulp layer of the nonwoven fabric faced the polyethylene film and the rayon veneer layer faced outwardly of the bicomponent laminate.

A quantity of the aforementioned polyurethane adhesive was then applied to a second sheet of silicone release paper at the rate of 7 g/m$^2$ using a hand-held No. 200 gravure coating roller also obtained from Modern Engraving and Machine Company. The adhesive was then immediately transfer-coated onto an apertured polyethylene plastic net-like material available from Applied Extrusion Technologies, Inc. as Delnet* P530. Preferably, the Delnet had first been corona treated. The Delnet* P530 had a weight of about 0.55 oz/yd$^2$ (19 g/m$^2$); a thickness of about 4.3 mils (169 micrometers); an open area of 34%; and a Frazier air permeability of 705 ft$^3$/min-ft$^2$ (215m$^3$/min-m$^2$). The machine direction strip tensile strength of the Delnet material was about 4.9 lb/in width (0.86 kN/m) and the cross machine direction strip tensile strength was about 2.1 lb/in (0.37 kN/m). The Delnet* P530 comprised a series of hexagonal bosses connected by rib-like strands defining apertures or open regions therebetween. There were 20 bosses per inch in the machine direction and 38 bosses per inch in the cross direction. The area of an individual hexagonal boss was about 0.0038 in$^2$ (0.025 cm$^2$).

The adhesive-coated Delnet material was then hand laminated, again using light pressure, to the outer surface of the above-described bicomponent laminate to form a tricomponent laminate having a lower layer of liquid impermeable polyethylene film, an inner or core layer of absorbent nonwoven fabric and an upper layer of the Delnet P530 material. The assembled tricomponent laminate was allowed to dry for 24 hours at room temperature. The tricomponent laminate described above was then tested for absorbency, linting characteristics, and wet delamination resistance of the Delnet* material. The bicomponent laminate described in this Example 1 (which corresponds to the tricomponent laminate of the invention but without the Delnet* material layer) was used as a control.

Absorbency Test

Absorbency was tested according to the following procedure. A specimen 12"×10" (31 cm)×(25 cm) was clipped in place on a 45° inclined plane made of rigid plastic sheet, with the 12 inches (31 cm) direction Paralleling the length of the inclined plane. A 0.9% by weight aqueous solution of sodium chloride was prepared and added to a 100 ml burette. The tip of the burette was positioned at a distance of 5.0 cm from the surface of the specimen to be tested and at a point which was 25 cm from the bottom edge of the mounted sample. The saline solution was allowed to flow at a rate of about 0.7 ml/s from the burette onto the upper surface of the material to be tested. Flow of saline solution was stopped when the advancing front of the saline solution reached the lower edge of the material being tested. The absorbent capacity in milliliters was taken as the difference between the amount of saline in the burette at the start of the test (i.e 100 ml) and the amount remaining in the burette at the end of the test. The time elapsed from the start of the test until the end was measured with a stop watch and recorded. The rate of absorbency is taken as the absorbent capacity (as defined above) divided by the elapsed time and is reported in ml/s.

The tricomponent laminate of Example I and the bicomponent laminate (i.e. the tricomponent laminate without the Delnet* facing) were tested for absorbency with the following results:

|  | Absorbent Capacity, ml | Rate of Absorbency, ml/s. |
| --- | --- | --- |
| Tricomponent laminate of the invention | 20 | 1.0 |
| Bicomponent laminate control | 27 | 1.0 |

From the above test results it is seen that the absorbent capacity of the tricomponent laminate of the invention was about 25% less than that of the control. The rate of absorbency was the same, i.e. 1.0 ml/s., for both the laminate of the invention and the control. This was surprising in that the upper layer of the tricomponent laminate of the invention comprised the Delnet* material, whose open area was only about 34%.

Linting Test

Linting characteristics were determined by an Emergency Care Research Institute (ECRI) Test Method described in Health Devices, Vol. 15, No. 5, May 1986, the disclosure of which is incorporated herein by reference. In this test, the material to be tested for linting characteristics is subjected to cycles of abrasion and flexing.

Particles that are generated when a specimen is abraded and flexed are counted with the aid of a particle counter (Climet Model #8060). The counter is capable of counting particles >0.3 μm and >10 μm at a flow rate of 0.25 CFM. The test specimen consists of a reinforcing material and test fabric measuring 4 1/2"×6" (11 cm)×(15 cm) and 10"×11" (25 cm)×(28 cm), respectively, cut in the machine direction. The reinforcing fabric is positioned inside the test fabric and folded around a steel plate. The stationary lower specimen containing the test specimen is abraded against the mobile upper test specimen for a five minute period of time. The particle counter records the number of particles >0.3 μm and >10 μm during each minute. The average particles and standard deviation, for the number of particles >0.3 μm and >10 μm up to five minutes, is recorded.

Wet Delamination Resistance Test

The tricomponent laminate of Example 1 was tested to determine the resistance to wet delamination of the Delnet* porous netting material. The wet delamination test measures the force required to separate the Delnet* netting material from the underlying liquid absorbent nonwoven material A 1"×6" (2.5 cm × 15 cm) sample of the material to be tested is immersed in water for three (3) minutes. The sample is prepared for testing by separating the Delnet* material from the underlying liquid absorbent nonwoven material for a distance of about 1" (2.5 cm). An Instron Tensile Tester is used for the test. The free end of the Delnet* netting material is placed in one of the Instron jaws, while the free end of the remainder of the sample (in this case, the liquid-absorbent nonwoven fabric/liquid impermeable polyethylene film combination) is placed in the other jaw of the Instron. The test specimen is adhered to a 2"×6" (5.1 cm × 15 cm) steel plate using masking tape to keep the angle of force constant during the test procedure. The Instron jaws are separated at a rate of 12"/min. (31 cm/min). The force in grams which is required to completely delaminate the Delnet* netting is recorded for each test specimen.

Results of the tests are given below, where the values tabulated are averages.

| Sample Description | Absorbency (ml saline) | ECRI Linting > 0.3μ | > 10μ | Wet Delamination Resistance (g) |
|---|---|---|---|---|
| Tricomponent Laminate of the invention - Example 1 | 19.6 | 3018 | 14.6 | 80 |
| Control | 4.5 | 405,478 | 318 | — |

From the test results given above, it can be seen that the tricomponent laminate of the invention has vastly reduced linting characteristics and substantially improved saline absorbency when compared to the control, an extrusion-laminated (rather than adhesion-laminated) bicomponent laminate. The wet delamination resistance of the inventive tricomponent laminate is sufficiently high to avoid delamination during actual use.

Example II

Tricomponent laminates in accordance with the present invention were made with Delnet* plastic netting materials having open areas of 34%, 41% and 60%, since adequately high absorbency dictates a preference for open areas in excess of 30%. A bicomponent laminate (i.e. an adhesion laminate of liquid impermeable film and liquid absorbent nonwoven fabric but no Delnet* material) was used as a control. The Plastic film, nonwoven fabric, room-temperature curable polyurethane adhesive and method of preparation were the same for this Example II as those reported earlier herein for Example I. The adhesive was applied with a No. 200 gravure coating roller (Modern Engraving and Machine Co.) having a series of quadrangular depressions formed therein. These depressions had a length of 0.127 mm on each side and a depth of about 0.025 mm. There were 200 cells per inch (79/cm) measured on the diagonal.

The results of testing were as follows (values represent, in each case, the average of six readings):

| Sample | Open Area of Delnet* Netting Material | Absorbent Capacity (ml) | Rate of Absorbency (ml/s) | Linting (> 0.3μ) | Wet Delamination Resistance (g) |
|---|---|---|---|---|---|
| 1 | 34% | 20 | 1.0 | 7559 | 110 |
| 2 | 41% | 22 | 1.05 | 4468 | 54 |
| 3 | 60% | 21 | 1.0 | 4579 | 35 |
| Control | — | 28 | 1.0 | 405,478 | — |

All samples showed substantial reduction in linting, without any significant loss of absorbent capacity or absorbency rate.

I claim:

1. A laminated reinforcing panel for a surgical drape, comprising
   (a) a first outer layer that is liquid impermeable,
   (b) an absorbent intermediate layer that overlies the first outer layer,
   (c) a second outer layer that overlies the intermediate layer and is adhered to the intermediate layer by a cold cure adhesive, the second outer layer comprising a plastic web structure of spaced-apart bosses interconnected with strands, with the remaining area being open.

2. The panel of claim 1 in which the first outer layer comprises polyethylene film.

3. The panel of claim 1 in which the first outer layer comprises a corona-treated film.

4. The panel of claim 1 in which the intermediate layer comprises a nonwoven fabric.

5. The panel of claim 1 in which the intermediate layer incorporates an antimicrobial agent 6. The panel of claim 1 in which the second outer layer comprise a nonwoven plastic.

7. The panel of claim 1 in which the second outer layer comprises a corona-treated plastic.

8. The panel of claim 1 in which the open area in the second outer layer comprises at least about 30% of its total area.

9. The panel of claim 1 in which the adhesive is a moisture-cured polyurethane adhesive.

10. The panel of claim 9 in which the adhesive has a microfiber structure.

11. The panel of claim 9 in which the adhesive forms a dot pattern surrounded by adhesive-free areas, the adhesive covering less than half the total area.

12. A surgical drape having a top surface and a bottom surface and having secured to its top surface, in a region within which surgery is to be performed, the first outer layer of the panel of any of claims 1-7.

13. The drape of claim 12, further comprising a fenestration cut through the reinforcing panel and drape to provide access through the drape within the area covered by the reinforcing panel.

* * * * *